United States Patent [19]

Eckenhoff

[11] Patent Number: 5,137,727
[45] Date of Patent: * Aug. 11, 1992

[54] DELIVERY DEVICE PROVIDING BENEFICIAL AGENT STABILITY

[75] Inventor: James B. Eckenhoff, Los Altos, Calif.
[73] Assignee: ALZA Corporation, Palo Alto, Calif.
[*] Notice: The portion of the term of this patent subsequent to Jul. 23, 2008 has been disclaimed.
[21] Appl. No.: 714,415
[22] Filed: Jun. 12, 1991
[51] Int. Cl.$^5$ .............. A61K 9/20; A61M 31/00
[52] U.S. Cl. .............. 424/422; 424/423; 424/426; 424/473; 424/484
[58] Field of Search ............. 424/422, 438, 473

[56] References Cited

U.S. PATENT DOCUMENTS

| | | | |
|---|---|---|---|
| 3,845,770 | 11/1974 | Theeuwes et al. | 128/260 |
| 3,865,108 | 2/1975 | Hartop | 128/260 |
| 3,916,899 | 11/1975 | Theeuwes et al. | 128/260 |
| 3,995,632 | 12/1976 | Nakano et al. | 128/260 |
| 4,002,173 | 1/1977 | Manning et al. | 128/296 |
| 4,063,064 | 12/1977 | Saunders et al. | 219/121 |
| 4,088,864 | 5/1978 | Theeuwes et al. | 219/121 LM |
| 4,111,202 | 9/1978 | Theeuwes | 128/260 |
| 4,111,203 | 9/1978 | Theeuwes | 128/260 |
| 4,200,098 | 4/1980 | Ayer et al. | 128/260 |
| 4,203,439 | 5/1980 | Theeuwes | 128/260 |
| 4,207,893 | 6/1980 | Michaels | 128/260 |
| 4,285,987 | 8/1981 | Ayer et al. | 427/3 |
| 4,327,725 | 5/1982 | Cortese et al. | 128/260 |
| 4,526,938 | 7/1985 | Churchill et al. | 525/415 |
| 4,612,008 | 9/1986 | Wong et al. | 604/892 |
| 4,772,474 | 9/1988 | Eckenhoff | 424/473 |
| 4,874,388 | 10/1989 | Wong et al. | 604/891.1 |
| 5,034,229 | 7/1991 | Magruder | 424/473 |
| 5,057,318 | 10/1991 | Magruder | 424/438 |
| 5,059,423 | 10/1991 | Magruder | 424/438 |

OTHER PUBLICATIONS

Nucleic Acid Res., 10:7197 (1982).
Arch. Biochem. Biophys., 156:493 (1973).
DNA 2:37 (1983).

Primary Examiner—Thurman K. Page
Assistant Examiner—Raj Bawa
Attorney, Agent, or Firm—Jacqueline S. Larson; Edward L. Mandell; Steven F. Stone

[57] ABSTRACT

The present invention is directed to an improved fluid-imbibing dispensing device for delivering a beneficial agent to a biological environment of use, the dispensing device being of the type having a housing which includes a fluid-impermeable first wall section with an open end and a fluid-permeable second wall section with an open end, an internal compartment formed by the first and second wall sections, exit means in the housing, a beneficial agent in that portion of the compartment formed by the first wall section, expandable driving means in that portion of the compartment formed by the second wall section, and a partition layer between the beneficial agent and the expandable driving means; wherein the improvement comprises the first wall section being comprised of an extremely fluid-impermeable material and the open end of each of the first wall section and the second wall section having reciprocally tapered edges one with the other to form a tapered lap joint for mating engagement, the tapered lap joints being bonded together with a pressure-sensitive contact adhesive to form the housing.

22 Claims, 1 Drawing Sheet

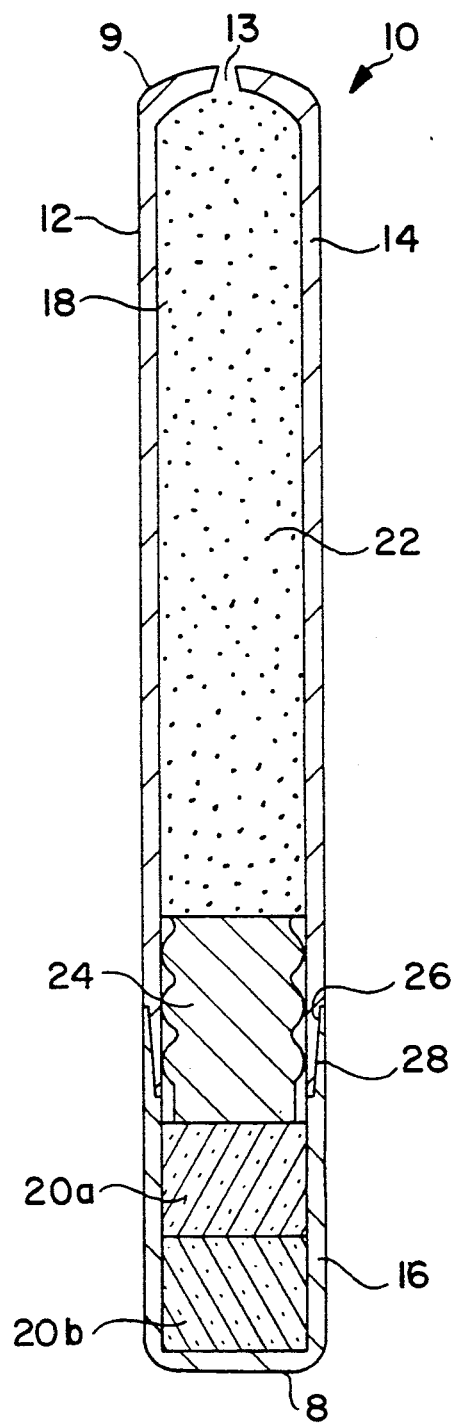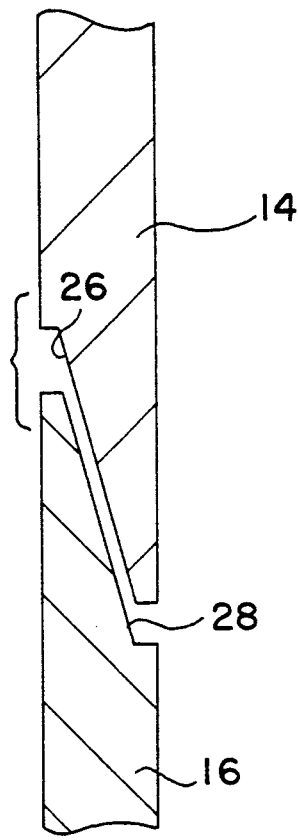

DELIVERY DEVICE PROVIDING BENEFICIAL AGENT STABILITY

FIELD OF THE INVENTION

This invention relates to an active agent delivery device. More particularly, the invention relates to a delivery device that is provides stability for fluid-sensitive beneficial agents.

BACKGROUND OF THE INVENTION

Delivery devices for administering a beneficial agent to a biological fluid environment of use are known in the prior art. Representative examples of various types of delivery devices are disclosed in U.S. Pat. Nos. 3,845,770; 3,916,899; 3,995,632; 4,111,202; 4,111,203; 4,203,439; 4,327,725; and 4,612,008; al of which are incorporated herein by reference. The delivery devices described in the above patents operate successfully for their intended use and they can deliver many beneficial agents for their intended effects. However, it has been observed that their use can be limited because they lack the necessary elements to deliver beneficial agents that are sensitive to fluids and to fluids containing biological gases. Their use may be limited because beneficial agents that are sensitive to such aqueous biological fluids or to other fluids external to the delivery device may be adversely affected by fluids that enter the device and contact the beneficial agents during operation of the device. Examples of such fluid-sensitive agents include proteins, peptides, and hormones. Moreover, the prior art devices lack the necessary means for their use as implant devices for dispensing such sensitive agents to a biological fluid-rich environment of use.

To overcome the limitations associated with the prior art delivery devices, a delivery device was developed and is described and claimed in copending, commonly-assigned patent application U.S. Ser. No. 07/283,359, filed Dec. 13, 1988, now issued as U.S. Pat. No. 5,034,229 to Magruder et al. for Delivery System Comprising Means for Governing Fluid Ingress into the System. This delivery device comprises a compartment, one portion of which is substantially impermeable to fluid and contains a fluid-sensitive drug protected from a fluid environment, and a second portion of which is permeable to fluid and contains an expandable driving means for administering the drug to the fluid environment of use. The system has been found to be particularly useful as an implant in livestock for delivering a fluid-sensitive drug over a broad range of dosage delivery rates according to a predetermined time-release pattern.

A disadvantage recently discovered with the devices of U.S. Pat. No. 5,034,229 is that, in order for the drug reservoir portion and the fluid-permeable portion of the device to be adhesive bonded at their lap joints to produce a hydrostatically intact seal under internal back pressure up to 15 psi, the materials of the two portions must dissolve in similar solvents. A simple pressure-sensitive adhesive will not provide an adequate seal between the straight edges of the two portions. As a consequence of this limitation, the materials which must be used for the drug reservoir, in order to form an adhesive bond seal with the dimensionally unstable and thin fluid-permeable membrane, must have, in fact, a finite osmotic permeability to water. At the same time, certain stable and resorbable somatotropin formulations to be delivered are osmotically active, having the same osmotic activity as a saturated solution of sodium chloride; additionally, these agents, as well as other proteins and peptides, are labile and will aggregate in the presence of water. The combination of these characteristics results in absorption of some water through the reservoir wall and dilution and some inactivation of beneficial agent inside the reservoir. In vitro and in vivo testing results from prior art devices according to U.S. Pat. No. 5,034,229 have demonstrated up to 20–25% dilution of a somatotropin fluid-sensitive beneficial agent formulation at 4–5 weeks of delivery.

Accordingly, it is desirable to provide a delivery device that provides improved stability for the benficial agent formulation in vivo; that is, it does not cause the dilution and inactivation of an active agent to be delivered by the device.

SUMMARY OF THE INVENTION

It has now been discovered by the inventor that when the open ends of the two portions or sections making up the housing of the devices of U.S. Pat No. 5,034,229 are a certain configuration other than those illustrated in U.S. Pat. No. 5,034,229, the two portions can be joined together and bonded with simple contact adhesive compositions which do not require dissolution of the materials of the portions by a common solvent. This is accomplished by the open ends of the fluid-impermeable and the fluid-permeable sections having reciprocally tapered edges one with the other to form a tapered lap joint for mating engagement of the two sections. When the tapered lap joints are joined together with a pressure-sensitive contact adhesive, the resulting bond provides a hydrostatically intact seal.

Such a tapered lap joint makes it possible to utilize extremely fluid-impermeable materials in the manufacture of the beneficial agent reservoir to provide stability for fluid-sensitive beneficial agents in a fluid environment of use.

Thus, the present invention is directed to an improved fluid-imbibing dispensing device for delivering a beneficial agent to a biological environment of use, the dispensing device being of the type having a housing which includes a fluid-impermeable first wall section with an open end and a fluid-permeable second wall section with an open end, an internal compartment formed by the first and second wall sections, exit means in the housing, a beneficial agent formulation in that portion of the compartment formed by the first wall section, expandable driving means in that portion of the compartment formed by the second wall section, and a partition layer between the beneficial agent formulation and the expandable driving means; wherein the improvement comprises the first wall section being comprised of an extremely fluid-impermeable material and the open end of each of the first wall section and the second wall section having reciprocally tapered edges one with the other to form a tapered lap joint for mating engagement, the tapered lap joints being bonded together with a pressure-sensitive contact adhesive to form the housing.

BRIEF DESCRIPTION OF THE DRAWINGS

FIG. 1 is a cross-sectional view of one embodiment of the present invention.

FIG. 2 is an enlarged view of a portion of the housing walls of the device of the present invention showing the tapered lap joint at the ends of each of the wall sections of the housing and their relation to each other.

DETAILED DESCRIPTION OF THE INVENTION

In the following discussion, like reference numerals refer to like elements in the figures.

FIG. 1 illustrates in cross-sectional view one embodiment of the delivery device according to the present invention. Delivery device 10 comprises a housing 12 formed of a first wall section 14 and a second wall section 16. Housing 12 surrounds and defines an internal compartment 18. Delivery device 10 has at least one exit passageway 13 for delivering a beneficial agent formulation from device 10. Optionally, the exit passageway can be occluded with a material that is discharged, leaches or erodes during the time of use. In FIG. 1, housing 12 comprises a dome-shaped or rounded rear end 8 and a similar dome-shaped or rounded lead end 9 for aiding in placing delivery device 10 in an animal host. In an embodiment not shown, delivery system 10 can be manufactured with a pair of flat ends 8 and 9. The term "lead end", as used herein, generally denotes the end from which beneficial agent is released from the device. In use, either the lead end or the rear end may be implanted first. First wall section 14 defines lead end 9, it forms passageway 13 and it surrounds that portion of internal compartment area 18 which contains a beneficial agent formulation 22. First wall section 14 at its end distant from lead end 9 defines and forms an open end having a tapered edge forming a tapered lap joint 26. Second wall section 16 defines rear end 8 and it surrounds that portion of internal compartment 18 which contains the expandable driving means, here illustrated by two expandable driving members 20a and 20b, for expanding and for occupying space in compartment 18 for delivery of a beneficial agent formulation from delivery device 10. While two driving members are shown in this embodiment, it is to be understood that this number is not controlling and that any number of driving members may make up the driving means. Second wall section 16 at its end distant from rear end 8 defines and forms an open end having a tapered edge forming a tapered lap joint 28.

Tapered lap joints 26 and 28 are reciprocally tapered one with the other for mating engagement when the two edges are assembled together. FIG. 2 shows in greater detail the two tapered lap joints and their relation to each other at the point of joinder. The tapered lap joints 26 and 28 are of such a design as to provide a strong and hydrostatically intact seal when they are bonded together with a pressure-sensitive contact adhesive. While FIG. 1 shows the two wall sections assembled with the tapered lap joint 26 of first wall section 14 inserted into the inside of the tapered lap joint 28 of second wall section 16, this arrangement is not critical and may be reversed.

Compartment 18 comprises a beneficial agent formulation 22. Compartment 18 further optionally, and preferably, comprises a partition layer 24 which is positioned between the beneficial agent formulation 22 and the expandable driving member 20a. Partition layer 24, in a presently preferred embodiment, comprises a composition that is substantially impermeable to the passage of fluid, and it serves to restrict the passage of fluid present in the expandable driving member into the beneficial agent formulation. It operates to essentially maintain the integrity of the beneficial agent formulation layer and the driving means. Partition layer 24 acts also to insure that the expanding driving force generated by the expandable driving members 20a and 20b is applied directly against the beneficial agent formulation 22.

In operation, as the expandable driving members 20a and 20b absorb and imbibe fluid through second wall section 16 from the environment of use, they expand and push against partition layer 24, causing it to slide inside compartment 18. As the driving members continue to expand into compartment 18, partition layer 24 moves towards exit passageway 13, pushing the beneficial agent formulation 22 through passageway 13 for maximizing the delivery of the beneficial agent to a biological environment of use, such as livestock.

First wall section 14, which surrounds the internal space of compartment 18 initially occupied by the beneficial agent formulation 22, comprises a composition that does not adversely affect the beneficial agent or other ingredients in delivery device 10, the host, or the like. First wall section 14 is formed of a composition comprising means that is extremely fluid-impermeable and substantially prevents the passage of an external fluid into device 10. The phrases "substantially prevents" and "extremely fluid-impermeable", as used herein, indicate that the compositions for forming first wall section 14 should be of sufficient impermeability to fluids that the amount of fluid from the environment of use which can pass through the first wall section is insignificant to cause degradation or inactivation of a fluid-sensitive beneficial agent during the period of use. Materials (such as the polycarbonates) which dissolve in the same or similar solvents as the fluid-permeable materials of second wall section 16 do not meet this requirement since, by their nature, they are somewhat permeable to fluids. However, prior to the present invention, other more fluid-impermeable materials could not be used for first wall section 14 because they could not form an acceptable solvent bond with the materials of second wall section 16, while adhesive bonding did not provide a seal of sufficient strength and water-impermeability. It has now been found that, as a result of the particular modification of the lap joints that is the basis of the present invention, an improved delivery device is possible that incorporates a first wall section of extremely fluid-impermeable material.

Typical impermeable compositions for forming first wall section 14 are, for example, vinylidene chloride copolymers and terpolymers such as vinylidene chloride-vinyl chloride copolymer, vinylidene chloride-acrylonitrile copolymer, vinylidene chloride-styrene copolymer, and vinylidene chloride-vinyl chloride-acrylonitrile terpolymer; acrylonitrile polymers such as acrylonitrile-methyl vinyl ether copolymer, acrylonitrile-styrene copolymer, acrylonitrile-butadiene-styrene terpolymer, and the like; halogenated polymers such as chlorinated polyether, tetrafluoroethylene and hexafluoropropylene copolymer, polyvinylfluoride, polyvinyl-chlorobuteral, plasticized polyvinylidene chloride, and the like; nylon; polyamide-imide; polyarylether; polyurethane; polyolefinics such as high density polyethylene, polypropylene, polytetrafluoroethylene, polydichloroethylene, polychlorotrifluoroethylene, and the like; polyvinylchloride-acrylic copolymer; glass; bakelite; melamine; polyethylene terephthalate; polyacrylate; stainless steel and stainless steel mesh; and the like. The polyolefinics are presently preferred, and polypropylene is more preferred. The polyolefinic materials have at least about 100 to 1000 times less water permeability than the polycarbontes, a preferred material for the first wall section in U.S. Pat. No. 5,034,229. The various polymers are known in the *Handbook of Common Polymers*, by Scott and Roff, CRC Press, Cleveland Rubber Co., Cleveland, Ohio.

To further reduce or limit permeability of the compositions making up first wall section 14, impermeable particulate fillers known to the industry, such as, for example, titanium dioxide and mica flakes, or homogeneous polymer alloys and barriers are within the scope of this invention and can be used to form first wall section 14.

Because the expandable driving means, exemplified in FIG. 1 by expandable driving members 20a and 20b, operates by the imbibition of external fluid, second wall section 16 in at least a portion that is adjacent to the expandable means must comprise a composition that is permeable to the passage of external fluids such as water and biological fluids, and is substantially impermeable to the passage of beneficial agents, osmopolymers, osmagents, and the like. Typical compositions comprising semipermeable materials for forming wall 16 are known in the art. In one presently preferred embodiment, they are a member selected from the group consisting of a cellulose ester, a cellulose ether and a cellulose ester-ether. These cellulosic polymers have a degree of substitution, D.S., on the anhydroglucose unit from greater than 0 up to 3, inclusive. By degree of "substitution" or "D.S" is meant the average number of hydroxyl groups originally present on the anhydroglucose unit comprising the cellulose polymer that are replaced by a substituting group. Representative fluid-permeable materials are discussed in U.S. Pat. No. 4,874,388, for example, the entire disclosure of which is incorporated herein by reference.

First wall section 14 and second wall section 16 optionally comprise a nontoxic plasticizer. Representative plasticizers suitable for forming wall 14 and wall 16 include plasticizers that lower the temperature of the second-order phase of transition or the elastic modulus of a composition. Also, the plasticizers increase the workability of wall 14 and wall 16 and their flexibility. Plasticizers operable for the present purpose include straight-chain and branched-chain plasticizers, cyclic plasticizers, acrylic plasticizers and heterocyclic plasticizers. Representative plasticizers are well known in the art, examples of which are disclosed in U.S. Pat. No. 4,874,388.

Housing 12, comprising wall sections 14 and 16, is nontoxic, biologically inert, nonallergenic and nonirritating to body tissue, and it maintains its physical and chemical integrity; that is, housing 12 does not erode or degrade in the environment of use during the dispensing period. It is within the scope of the invention that the housing be insoluble only during the period of intended use and can thereafter dissolve away in the environment of the device. Thus, a dispenser is here contemplated which is unaffected by its environment, solubility-wise, at the situs of use or which, alternatively, is only slightly soluble during the period of intended use, such that once its active agent content has been removed it will then dissolve or erode away leaving no objectionable residue or empty container at the situs of use. Additionally, housing 12, comprised of wall sections 14 and 16, is rigid; that is, it retains its shape and is inflexible so that it does not bend or otherwise deform as a result of transient mechanical forces.

Delivery device 10 comprises a beneficial agent formulation 22 that produces a desired and useful result when administered to a warm-blooded animal, including humans and farm animals. The term "beneficial agent formulation", as used herein, comprises the active or beneficial agent to be delivered, generally in a carrier substance and with or without additional inert ingredients. The pharmaceutically acceptable carrier useful herein may comprise more than one ingredient, such as, for example, a buffer, a viscosity-regulating vehicle, a surfactant, dyes, a permeation enhancer, proteinase inhibitors, or other formulation ingredients and additives, as are known in the art.

The beneficial agent in formulation 22 is useful in one embodiment for increasing the rate of growth and the efficiency of feed utilization in equine, bovine and swine. The beneficial agent in another embodiment is useful for controlling estrus and ovulation in the course of breeding farm animals for commercial purposes, for effecting contraception and for producing an anabolic response associated with the inhibition of estrus. Beneficial agent in another embodiment is a drug useful for producing a therapeutic effect. The beneficial agent in yet other embodiments comprises agents that act at synaptic and neuroeffector sites, agents acting on the central nervous system, autocoids, anti-inflammatory agents, analgesics, antipyretic agents, cardiovascular agents, and the like.

The terms "active agent", "beneficial agent" and "drug" are used interchangeably herein and refer to an agent, drug, compound, composition of matter or mixture thereof which provides some therapeutic, often beneficial, effect. Representative beneficial agents that can be administered by delivery device 10 include pharmacologically active peptides and proteins, anabolic hormones, growth promoting hormones, hormones related to the endocrine system comprising porcine growth promoting hormone, bovine growth promoting hormone, equine growth promoting hormone, ovine growth promoting hormone, human growth promoting hormone, growth promoting hormones derived by extraction and concentration from pituitary and hypothalmus glands, growth promoting hormones produced by recombinant DNA methods, bovine growth promoting hormone as described in *Nucleic Acid Res.*, 10:7197 (1982), ovine growth promoting hormone as described in *Arch. Biochem. Biophys.*, 156:493 (1973), and porcine growth promoting hormone as described in *DNA*, 2:37 (1983). The polypeptides also comprise growth hormone, somatropin, somatotropin, somatotropin analogues, modified porcine somatotropin, modified bovine somatotropin, derivatives of somatotropin including both porcine and bovine somatotropin derivatives, somatomedin-C, gonadotropic releasing hormone, follicle stimulating hormone, luteinizing hormone, LH-RH, growth hormone releasing factor, gonadotropin releasing factor, insulin, insulin-like growth factor, colchicine, chorionic gonadotropin, oxytocin, somatotropin plus an amino acid, vasopressin, adrenocorticotrophic hormone, epidermal growth factor, fibroblast growth factor, platelet-derived growth factor, transforming growth factor, nerve growth factor, prolactin, somatostatin, somatotropin plus a protein, cosyntropin, lypressin, polypeptides such as thyrotropin releasing hormone, thyroid stimulating hormone, secretin, pancreozymin, enkephalin, glucagon, interleukin-1, interleukin-1 receptor antagonist, superoxide dismutase, endocrine agents secreted internally and distributed in an animal by way of the bloodstream, and the like.

The amount of active or beneficial agent employed in the delivery device of the invention will be that amount necessary to deliver a therapeutically effective amount of the agent to achieve the desired result at the site of delivery. In practice, this will vary widely depending upon such variables as the particular agent, the site of delivery, the severity of the condition, and the desired therapeutic effect, for example. Thus, it is not practical to define a particular range for the therapeutically effective amount of active agent incorporated into the device. Beneficial agents and their dosage unit amounts are known to the prior art in *The Pharmacological Basis of Therapeutics*, by Gilman, Goodman, Rall and Murad, 7th Ed., (1985), MacMillan Publishing Co., NY; in *Pharmaceutical Sciences*, Remington, 17th Ed., (1985), Mack Publishing Co., Easton, Pa.; and in U.S. Pat. No. 4,526,938. Other useful beneficial agents are discussed in U.S. Pat. No. 4,874,388.

As used herein, the term "therapeutically effective amount" refers to the amount of the active agent needed to effect the desired therapeutic result.

The expandable driving means, exemplified in FIG. 1 by expandable driving members 20a and 20b, operable for pushing the beneficial agent composition 22 from delivery device 10 comprises, in a presently preferred embodiment, an osmopolymer. The osmopolymers interact with water and aqueous biological fluids and swell or expand to an equilibrium state. The osmopolymers exhibit the ability to swell in water and to retain a significant portion of the imbibed and absorbed water within the polymer structure. In another preferred embodiment, the expandable driving means comprises an osmagent. The osmagents are known also as osmotically effective solutes and they are also known as osmotically effective compounds. The osmotically effective solutes that can be used for the purpose of this invention include inorganic and organic compounds that exhibit an osmotic pressure gradient across a semipermeable, i.e. a fluid-permeable, wall. The expandable driving means in yet another preferred embodiment comprises an optional osmagent dispersed within the osmopolymer. The osmagent or osmopolymer can be in any suitable form such as particles, crystals, pellets, granules, and the like, when pressed into a layer or a tablet and placed or pressed into second wall section 16. Osmagents and osmopolymers are known to the art in U.S. Pat. Nos. 3,865,108, 4,002,173, 4,207,893, 4,327,725 and 4,612,008, for example.

Partition layer 24, positioned between the beneficial agent composition and the expandable driving means, is a means for maintaining the separate identity of the beneficial agent composition and the driving means, for transmitting the force generated by the driving means against the beneficial agent composition, and for substantially restricting the passage of fluid between the beneficial agent composition and the driving means. Representative materials useful as a partition layer 24 are known to the art in, for example, U.S. Pat. No. 4,874,388.

The terms "exit means" and "exit passageway", as used herein, comprise means and methods suitable for the metered release of the beneficial agent 22 from compartment 18 of delivery device 10. The exit means 13 includes at least one passageway, orifice, or the like, through first wall section 14 for communicating with compartment 18. The expression "at least one passageway" includes aperture, orifice, bore, pore, porous element through which the agent can migrate, hollow fiber, capillary tube, porous overlay, porous insert, and the like. The expression also includes material that is discharged, erodes or is leached from the wall in the fluid environment of use to produce at least one passageway in delivery device 10. Representative materials suitable for forming at least one passageway, or a multiplicity of passageways, include an erodible poly(glycolic) acid or poly(lactic) acid member in the wall; a gelatinous filament; poly(vinyl alcohol); leachable materials such as fluid removable pore-forming polysaccharides, salts, or oxides; erodable or dischargable materials such as natural and synthetic waxes; and the like. The expression includes structural characteristics that concentrate stress at a precise point in the wall so that only a small amount of force will induce breakage in the wall, yielding a passageway through the wall from compartment 18 to the outside of the device. A passageway or a plurality of passageways can be formed by leaching a material such as sorbitol, lactose and like water-soluble solids from the wall. A passageway or passageways can be formed by the discharge, as a result of the pressure created by the expandable driving means for example, of a material such as a wax. The exit means or passageway can have any shape such as round, triangular, square, elliptical, and the like, for assisting in the metered release of beneficial agent from delivery device 10. Delivery device 10 can be constructed with one or more passageways in spaced-apart relations or more than a single surface of a dosage form. Passageways and equipment for forming passageways are disclosed in U.S. Pat. Nos. 3,845,770; 3,916,899; 4,063,064; and 4,088,864. Passageways formed by leaching are disclosed in U.S. Pat. Nos. 4,200,098 and 4,285,987.

Delivery device 10 can be manufactured by standard manufacturing techniques. In one process, the first wall section 14 and the second wall section 16 are independently injection molded or extruded into the desired shape. Then, the first wall section 14 is filled with the beneficial agent composition 22. The second wall section 16 is then filled with an expandable driving member or members, and the partition layer 24 is added thereto in layered arrangement. Optionally, the partition layer may be added to the first wall section 14 after filling the wall section with beneficial agent, in addition to, or instead of, the partition layer added to second wall section 16. Next, a pressure-sensitive contact adhesive is applied onto the tapered edge or lap joint of the open end of one or both of the first and second wall sections, by spraying or roller coating for example, and the two sections at their open ends are slid together and sealed at their reciprocally tapered lap joints. Then, at least one exit passageway 13 is drilled in the lead end 9 of the manufactured assembly. Alternately, the exit passageway can be preformed, such as during the injection molding of first wall section 14. Optionally, a passageway is drilled or preformed in the wall and sealed with a break-off tab that is broken open, or cut open, or the like, at the time of use to connect through the passageway the beneficial agent composition 22 with the exterior of delivery device 10. Or, the drilled or preformed passageway is sealed by a material that is discharged, leaches, erodes, or dissolves, for example, in the environment of use.

Pressure-sensitive adhesives which are useful in the present invention include, but are not limited to, silicone adhesive, D3 PIB adhesive, and acrylate adhesive.

These adhesives are advantageous over the cyanoacrylate solvent-adhesives used in the manufacture of the prior devices of U.S. Pat. No. 5,034,229 because they eliminate a period of time required for curing during manufacture. Additionally, these pressure-sensitive adhesives are especially advantageous as they resist shear forces in a longitudinal direction.

The delivery device of the present invention can be manufactured for delivering numerous beneficial agents, including drugs, at a controlled rate to a presently preferred biological environment of use such as warm-blooded animals, including humans; ruminants, such as bovines and sheep; porcines, such as hogs and swine; horses; and the like. The delivery devices provide for high loading of a beneficial agent and for its improved delivery in therapeutically effective amounts over time while providing resistance to transient mechanical forces. It is to be understood that the delivery devices can take a wide variety of shapes, sizes and forms adapted for delivering beneficial agents to environments of use. For example, the devices manufactured as delivery devices can be used for dispensing a beneficial agent in the anal-rectal passageway, in the cervical canal, as an artificial gland, in the vagina, as a subcutaneous implant, and the like. The delivery devices can be used in hospitals, nursing homes, outpatient clinics, sickrooms, veterinary clinics, farms, zoos, and other environments of use.

One embodiment of the invention pertains to a method for delivering a beneficial agent such as a drug to an animal. The method comprises implanting a delivery device, shaped, sized and adapted as an implant, into an animal, such as a muscle or an ear thereof. The method comprises the steps of: (a) admitting into an animal a delivery device of the present invention; (b) allowing fluid to be imbibed through the semipermeable second wall section of the delivery device for causing the expandable driving means to expand and push against the beneficial agent formulation; and (c) delivering the beneficial agent formulation from the delivery device by the expandable means increasing in volume at a controlled rate, thereby pushing the beneficial agent formulation to be delivered in an effective amount through the exit orifice to the animal over a prolonged period of time.

The implant can be implanted into receiving tissue using an implanter. Generally, an implanter comprises a tubular member with a central longitudinal axial bore, a pointed, elongated, annular concavely beveled implanting end and an implant-charging end. The implanting end and the charging end communicate through a bore. A plunger adapted to be removably inserted in the bore is designed for slidable movement therein for applying the necessary force for implanting the implant. Also, the implant can be surgically implanted in the muscle or other tissue of an animal.

EXAMPLE 1

A delivery device manufactured in the shape of an implantable delivery device as illustrated in FIG. 1 is manufactured as follows.

First, an expandable driving member is prepared by adding 7.6 kg of water and 0.4 kg of polyvinylpyrrolidone to a stainless steel container and mixing the components for 20 hours to obtain a smooth binder solution. Next, 10.0 kg of sodium Carbomer ®, a sodium salt of polyacrylic acid polymer, are sized by forcing through a 0.028 inch mesh screen in a fluid air mill set at 780-800 rpm spped, and 15.0 kg of sodium chloride are sized by forcing through a 0.028 inch mesh screen in the same manner. The screened polymer and sodium chloride are transferred to the granulator bowl of a fluid bed granulator, and 6.13 kg of binder solution is slowly sprayed onto the polymer and salt to form polymer/salt granules. These resultant granules are sized through a 16 mesh screen. The amount of granulation from the above steps is 25.2 kg, and this is transferred to a blender. An amount (0.255 kg) of magnesium stearate, a lubricant, is added to make up 1% of the total granulation including the lubricant. All ingredients are mixed together for minutes at 10 rpm to produce a homogeneous expandable driving composition. The composition next is pressed into the shape of osmotically active tablets in a tablet press at a pressure of 500 lbs to produce a round, flat-faced 50 mg tablet as an expandable driving member.

The semipermeable (fluid-permeable) second wall section that forms a compartment for containing the osmotically active tablet or tablets is prepared by first dry-blending 3.85 kg of cellulose acetate butyrate and 1.15 kg of tributyl citrate for five minutes. This produces a polymer/plasticizer blend of 77/23 ratio for the rate-controlling semipermeable wall. The blend is then fed into an injection molder and molded into the semipermeable second wall section forming a compartment with an open end for receiving an expandable driving member tablet or tablets and for mating the second section with the first wall section of the delivery device. The open end is formed with a tapered edge to create a tapered lap joint.

The fluid-impermeable first wall section, designed with an orifice in place, is prepared by feeding polypropylene neat into the hopper of an injection molder and molding the polypropylene into an impermeable first wall section forming a compartment with an open end for receiving components and for mating with the semipermeable second wall member. The open end is formed with a tapered edge or lap joint that is reciprocally tapered to the tapered lap joint of the semipermeable second wall section so that the two edges may be mated together. Next, the orifice channel is sealed with wax in the following manner. First, 142 gm of microcrystalline wax 180M and 142 gm of microcrystalline wax X145A are mixed together to effect a 50/50 blend of the two waxes, and the blend is melted and heated and held to 105°-115° C. for the ensuing operation. The lead end (with the orifice channel) is dipped into the melted wax blend for 20 seconds, then removed from the melted wax and cooled for at least 20 seconds, and the excess wax is then wiped off.

The elastomeric partition or piston is prepared by injection molding Santoprene ®, a thermoplastic elastomer, into a four-ribbed piston, weighing approximately 31 mg. The piston is then lubricated with silicone medical fluid 1000 cs to facilitate movement of the piston inside the device.

The delivery device is assembled by first charging the subassembly comprising the semipermeable second wall section with two of the expandable osmotic tablets. The lubricated elastomeric piston is then inserted on top of the osmotic tablets to be flush with the top of the semipermeable wall section. Next, the subassembly comprising the fluid-impermeable first wall section is filled with 340 mg of beneficial agent formulation at 40° C., wherein the formulation comprises 33.33 wt % (weight percent) porcine somatotropin, 4.53 wt % sodium phosphate monobasic, 28.47 wt % water, 33.0 wt % glycerol, and 0.67 wt % Tween-80. Then, the surface of the tapered lap joint of the semipermeable second wall section is spray-coated with AS-102 acrylate adhesive, and the two subassemblies are joined by sliding the two wall sections together at their reciprocally tapered lap joints to effect a sealed delivery device.

The novel devices of this invention use means for the obtainment of precise release rates in the environment of use while simultaneously maintaining the integrity of the device and the stability of the fluid-sensitive beneficial agent within the device. While there has been described and pointed out features of the invention as applied to presently preferred embodiments, those skilled in the art will appreciate that various modifications, changes, additions and omissions in the devices illustrated and described can be made without departing from the spirit of the invention.

What is claimed is:

1. An improved fluid-imbibing delivery device for delivering a beneficial agent to a biological environment of use, the dispensing device having a housing which includes a fluid-impermeable first wall section with an open end and a fluid-permeable second wall section with an open end, an internal compartment formed by the first and second wall sections, exit means in the housing, a fluid-sensitive beneficial agent formulation in that portion of the compartment formed by the first wall section, expandable driving means in that portion of the compartment formed by the second wall section, and a partition layer between the beneficial agent formulation and the expandable driving means; wherein the improvement comprises the first wall section being comprised of an extremely fluid-impermeable material and the open end of each of the first wall section and the second wall section having reciprocally tapered edges one with the other to form a tapered lap joint for mating engagement, the tapered lap joints being bonded together with a pressure-sensitive contact adhesive to form the housing.

2. A delivery device according to claim 1 wherein the first wall section is comprised of a polyolefinic material.

3. A delivery device according to claim 1 wherein the environment of use is an animal.

4. A delivery device according to claim 3 wherein the animal is a swine or a bovine.

5. A delivery device according to claim 1 wherein the beneficial agent formulation comprises a hormone.

6. A delivery device according to claim 1 wherein the first wall section comprises a polyolefinic material, and the beneficial agent formulation comprises a somatotropin, a somatotropin derivative or a somatotropin analogue.

7. A delivery device according to claim 1 wherein the device is an implant.

8. A delivery device according to claim 1 wherein the exit means comprises an exit passageway and means for closing the exit passageway.

9. A delivery device according to claim 8 wherein the means for closing the exit passageway is a material which is discharged, leaches or erodes.

10. A method for delivering a fluid-sensitive beneficial agent to an animal, wherein the method comprises:

(1) admitting into the animal an improved fluid-imbibing delivery device having a housing which includes a fluid-impermeable first wall section with an open end and a fluid-permeable second wall section with an open end, an internal compartment formed by the first and second wall sections, exit means in the housing, a fluid-sensitive beneficial agent formulation in that portion of the compartment formed by the first wall section, expandable driving means in that portion of the compartment formed by the second wall section, and a partition layer between the beneficial agent formulation and the expandable driving means; wherein the improvement comprises the first wall section being comprised of an extremely fluid-impermeable material and the open end of each of the first wall section and the second wall section having reciprocally tapered edges one with the other to form a tapered lap joint for mating engagement, the tapered lap joints being bonded together with a pressure-sensitive contact adhesive to form the housing;

(2) allowing fluid to be imbibed through the fluid-permeable second wall section of the dispenser for causing the expandable driving member to increase in volume; and (3) delivering beneficial agent to the animal by the driving member increasing in volume and occupying space in the internal compartment comprising the first wall section, thereby pushing the beneficial agent formulation through the exit means to the animal.

11. A method according to claim 10 wherein the first wall section comprises a polyolefinic material.

12. A method according to claim 10 wherein the animal is a swine or a bovine.

13. A method according to claim 10 wherein the beneficial agent formulation comprises a hormone.

14. A method according to claim 10 wherein the first wall section comprises a polyolefinic material, and the beneficial agent formulation comprises a somatotropin, a somatotropin derivative or a somatotropin analogue.

15. A method according to claim 10 wherein the device is an implant.

16. A method according to claim 10 wherein the exit means comprises an exit passageway and means for closing the exit passageway.

17. A method according to claim 16 wherein the means for closing the exit passageway is a material which is discharged, leaches or erodes.

18. A method for providing improved stability for a fluid-sensitive beneficial agent formulation in a fluid environment of use, which method comprises:

(1) admitting into the environment of use an improved fluid-imbibing delivery device having a housing which includes a fluid-impermeable first wall section with an open end and a fluid-permeable second wall section with an open end, an internal compartment formed by the first and second wall sections, exit means in the housing, a fluid-sensitive beneficial agent formulation in that portion of the compartment formed by the first wall section, expandable driving means in that portion of the compartment formed by the second wall section, and a partition layer between the beneficial agent formulation and the expandable driving means; wherein the improvement comprises the first wall section being comprised of an extremely fluid-impermeable material and the open end of each of the first wall section and the second wall section having reciprocally tapered edges one with the other to form a tapered lap joint for mating engagement, the tapered lap joints being bonded together with a pressure-sensitive contact adhesive to form the housing;

(2) allowing fluid to be imbibed through the fluid-permeable second wall section of the dispenser for causing the expandable driving member to increase in volume; and (3) delivering beneficial agent to the animal by the driving member increasing in volume and occupying space in the internal compartment comprising the first wall section, thereby pushing the beneficial agent formulation through the exit means to the animal.

19. A method according to claim 18 wherein the first wall section comprises a polyolefinic material.

20. A method according to claim 18 wherein the beneficial agent is a somatotropin, a somatotropin derivative or a somatotropin analogue.

21. A method according to claim 18 wherein the environment of use is an animal, and the animal is a swine or a bovine.

22. A method according to claim 18 wherein the device is an implant.

* * * * *